United States Patent [19]

Häfeli

[11] 4,259,447

[45] Mar. 31, 1981

[54] PROCESS FOR THE PRODUCTION OF UROKINASE IN PURE CONDITION

[75] Inventor: Robert Häfeli, Zürich, Switzerland

[73] Assignee: Alpha Patent Limited, Tel-Aviv, Israel

[21] Appl. No.: 53,552

[22] Filed: Jun. 29, 1979

[30] Foreign Application Priority Data

Jun. 30, 1978 [CH] Switzerland .................. 7197/78

[51] Int. Cl.³ ........................................... C12N 9/72
[52] U.S. Cl. ................................. 435/215; 435/815
[58] Field of Search ............................. 435/215, 815

[56] References Cited

U.S. PATENT DOCUMENTS

| 3,010,074 | 3/1977 | Uemura et al. | 435/215 |
| 4,066,506 | 1/1978 | Johnson et al. | 435/215 |
| 4,165,258 | 8/1979 | Pye | 435/215 |

OTHER PUBLICATIONS

Johnson et al., Analytical Biochemistry, vol. 72, pp. 573-576 (1976).
Chemical Abstracts, vol. 87, refernce 196465u (1977).
Chemical Abstracts, vol. 85, reference 173512b (1976).
Chemical Abstracts, vol. 85, reference 16039k (1976).

*Primary Examiner*—Lionel M. Shapiro
*Attorney, Agent, or Firm*—Cushman, Darby & Cushman

[57] ABSTRACT

There is provided a process for the production of pure, concentrated urokinase starting from a crude urokinase solution. The crude urokinase solution is contacted in a medium having a pH of $\geq 6$ with a porous solid matrix having a high specific surface area on whose surface there is immobilized aprotinin. Subsequently the urokinase adsorbed in this manner is eluted in an elution agent having a pH $\leq 4.5$. There are obtained highly concentrated and very pure solutions of urokinase. The urokinase is used in medicine as a pharmaceutical for the dissolving of fibrinous clots and coagulums.

35 Claims, No Drawings

PROCESS FOR THE PRODUCTION OF UROKINASE IN PURE CONDITION

BACKGROUND OF THE INVENTION

The present invention is directed to a new process for the production of pure urokinase.

Urokinase is a known enzyme which occurs in small amounts in the urine of mammals and accordingly also in human urine. Urokinase is an activator and serves to change plasminogen into plasmin. This enzyme in turn can dissolve fibrinous clots. Therefore urokinase preparations are valuable products in pharmaceutical medicine for the treatment, for example, of thromboembolisms.

There are known a number of processes for the isolation of urokinase from human urine and subsequent purification and concentration to a highly effective product. They consist of bringing the urine into contact with an adsorption agent and subsequently eluting the adsorbate. Then the crude urokinase is present in higher concentration in the extract. This extract in turn is worked up by means of various adsorption-elution and other separating processes so that finally there is obtained a highly concentrated and purified urokinase solution.

Known adsorption agents include for example calcium carbonate, barium sulfate, aluminum oxide, calcium phosphate, zinc hydroxide, activated carbon, hydrated aluminum silicates such as bentonite and kaolin, ion exchange silicates, molecular sieves as well as a number of other organic and inorganic materials.

In the meantime there have been proposed various affinity-chromatographic methods for the concentration and purification of urokinase. Most of these processes use for the affinitive adsorption solid matrices which e.g. contain the following compounds immobilized superficially: epsilon-aminocaproic acid and p-aminoenzamidine on Sepharose ®, antibody for urokinase on Sepharose, arginine on polyacrylamide resins, agmaline-epsiton-caproic acid on Sepharose ®, trypsin inhibitor on agarose, lysin or argenine on agaerose, trypsin inhibitor on Sepharose, urokinase inhibitor from human placenta on Sepharose and similar combinations.

On the other hand it is known to immobilize aprotinin on the surface of a solid matrix and to use the resin of this type which is prepared for the affinity-chromatographic separation and concentration of various compounds. However it is not known to use it with urokinase. For example in the Zeitschrift Biochimie 55, page 1323 (1973) there is described an affinity-chromatographic process for the concentration of trypsin on this kind of resin. A similar process is described in the same Zeitschrift in Volume 15, page 4 (1976). Furthermore there is described in the Journal of Physiological Chemistry 357, pages 1153 et seq. (1976) a process for the purification and characterization of human pancreaselastase. Finally note also the work in the Journal of Clinical Chemistry/Clinical Biochemistry, 15, pages 479 et seq. (1977) where there is described a process for the isolation of human kallikrein (callicrein).

SUMMARY OF THE INVENTION

While in the described state of the art it is known to immobilize urokinase by means of various compounds bound to the surface, however, aprotinin is specifically excluded, and likewise while it is known to immobilize aprotinin on solid matrices for the concentration and purification of various compounds, expressly excluding urokinase, it has now been surprisingly found that a separation and concentration of urokinase on aprotinin which is immobilized on solid materials leads to excellent and economically most favorable process results.

Before describing the true invention reference is made to the fact that in the known processes for production, the urokinase generally appears to be obtained in the form of two compounds, wherein the higher molecular weight compound has an average molecular weight of around 54,000 and the lower molecular weight compound has an average molecular weight of around 33,000. Surprisingly it has now been shown that the process of the invention to be described in further detail below there is obtained a urokinase whose average molecular weight only varies around an average value of approximately 54,000. The basis for this improvement of the product quality cannot yet be clearly explained, it is being investigated at present whether the urokinase with the lower average molecular weight is a breakdown product of the higher molecular weight.

The process of the invention for the production of pure urokinase of higher concentration and activity, starting from a crude urokinase solution prepurified and concentrated by known process is generally characterized by this urokinase crude solution in a medium with a pH of ≧6 being contacted with a porous solid matrix having a high specific surface area on which surface aprotinin is immobilized by means of covalent chemical bonds, that the carrier medium is separated and that subsequently the adsorbed urokinase is eluted by means of an eluting agent at pH≦4.5, whereupon there can be followed the known manufacturing methods for the production of various pharmaceutical preparations.

A special, industrially very important illustrative form of the above described process is characterized by the mentioned urokinase crude solution in a medium at pH≧6 being separated affinity-chromatographically in a column over a porous solid matrix having a high specific surface area on which surface aprotinin is immobilized by means of covalent chemical bonds and that subsequently the adsorbed urokinase of this type is eluted by means of an eluting agent at pH≦4.5.

The action of the immobilized aprotinin for the specific adsorption of urokinase is above all astonishing for the reason that aprotinin in solution at the usual concentrations is known not to inhibit the urokinase activity.

Besides resins surface activated with aprotinin compared to the present customary chromatography columns show a longer and more constant time of operation.

The urokinase crude solution employed should have a concentration of 2,000 to 10,000 international units (IU) urokinase per ml of solution, advantageously such a one with 3,000 to 5,000 IU urokinase per ml of solution as well as a purity of 200 to 2,000 IU urokinase per mg of protein present, advantageously such a one having 300 to 1,000 IU urokinase per mg of protein present.

As porous solid matrix there can be used various resins, for example, those based on polysaccharides, cellulose, agarose such as Sepharose of the Pharmacin AB, Sweden, dextran as for example Sephadex ® of the Pharmacin AB Sweden, or based on copolymer addition products based on polyacrylamides with agarose such as Sephacryl ® of the Pharmacin AB Sweden, or Ultrogen ® of LKB. It goes without saying that other solid matrices can also be employed, the main prerequisite is their capability to enter into covalent compounds with the aprotinin either directly or via bond facilitators. Such bond facilitators or spaces for example are epsilon-aminocaproic acid, in the international literature frequently designated by EACA (6-aminohexanoic acid), divinyl sulfone, various bis oxieranes or other compounds.

The solid matrix can, as frequently is the case with affinity-chromatography, be previously activated. For example, this can occur by means of BrCN or other known activating agents.

Again, it must be pointed out here that the process of the invention is not suited for working up of crude urine, the concentration of urokinase in this solution is too low. The mentioned crude urokinese solution can be brought to a total salt concentration of 0.5 to 1 mole by addition of various salts, for example NaCl or KCl.

Likewise before the true adsorption the adsorption agent, especially if it is present in a column, can be conditioned with a liquid medium at a pH of 6 to 9 and a total salt concentration of 0.5 to 1 mole. As buffers there can be used the known phosphate buffer (e.g. monopotassium phosphate-disodium phosphate) or tris buffer, but others can also be employed. As salts for the conditioning there can be added NaCl or KCl or other similar compounds.

After the actual adsorption of the urokinase on the solid matrix with the aprotinin and before the actual elution of the urokenase the laden solid matrix can be subjected to an intermediate rinsing. For this purpose there can be used a liquid agent with a 0.5 to 1 molar NaCl solution. Above all this intermediate washing serves for the removal of undesired proteins from the solid matrix. Washing with the agent can be continued until the agent on leaving is optically inactive at a wave length of 280 nm, i.e. shows practically no concentration of protein.

As eluting agent there can be used a solution of 0.5 to 1 molar NaCl or KCl. Since the elution according to the invention must be carried out at a pH $\leq 4.5$, there can be added, e.g. solutions of the above mentioned salts and concentrations at a pH of 2 to 4.5. Such solutions can be established, e.g., by addition of acetic acid or HCl, but other compounds can also be used.

To the elution agent there can also be added known elution aids such as aminoacids, e.g., aminocarboxylic acids such as lysine or arginine or others.

With the process of the invention there are attained solutions of urokinase which exhibit both high concentrations and also high purities of the urokinase. It is, e.g., not out of the question that with the process of the invention either in reference to the concentration and/or in reference to the purity of the urokinase there is attained in comparison to the starting material an improvement of a factor of about 100. By means of the process of the invention there can be obtained urokinase solutions which obtain purities of above 50,000 IU urokinase per mg protein present. Such purities today are considered generally as sufficiently high to be able to use the product directly in clinical insertions. In addition to the mentioned advantages there can be added the further previously mentioned fact that the pure urokinase produced according to the invention has a uniform molecular weight of about 50,000.

As illustration of the amounts and concentration values in the production of urokinase in general, below in the form of a table there are reproduced the various values for illustration.

TABLE

| Material | Process Step | Purity IU Urokinase per mg Protein | Yield [IU Urokinase] (based on 1 Liter Starting Solution | Volume [Liter] |
|---|---|---|---|---|
| Urine | | | 8,000 | 10,000 |
| | Adsorption | | | |
| Urokinase-Crude Solution | | 300 to 1,000 | 8,000 | 25 |
| | According to the Process of the invention | | | |
| Pure Concentrate | | 30,000 to 100,000 | 5,000 | Dependent on Process |
| | Depyrogenation, Other Processes | | | |

The process can comprise, consist essentially of or consist of the steps set forth and the compositions can comprise, consist essentially of or consist of the materials set forth.

Unless otherwise indicated all parts and percentages are by weight.

The process of the invention is further illustrated and explained by the examples.

DESCRIPTION OF THE PREFERRED EMBODIMENTS

EXAMPLE 1

500 ml of a crude urokinase solution containing $12 \times 10^6$ IU urokinase, i.e., with a concentration of 24,000 IU urokinase per ml of solution and a purity of 630 IU urokinase per ml of protein were percolated over a Sepharose-aprotinin column having a volume of one liter. The column was previously conditioned with a 0.1 molar tris-buffer to pH 8 [ tris-(hydroxymethyl)-amino-methane brought to pH 8 using hydrochloric acid]. Besides the mentioned conditioning liquid contained 0.5 molar NaCl. After the adsorption the same column was washed with the same conditioning liquid until the rinsing solution leaving showed an optical density at 280 nm of less than 0.100. Subsequently the column was rinsed with one liter of 0.5 molar NaCl solution.

The adsorbed urokinase was subsequently elutal with a solution of 0.5 molar NaCl, which was adjusted to a pH of 2.5 with HCl.

There were obtained 1.5 liters of eluate which in all contained 8,160,000 IU of urokinase (yield 68%). The purity of the thus obtained solution amounted to 53,000 IU urokinase per ml of protein present.

EXAMPLE 2

4.2 liters of a crude urokinase solution containing totally 22,260,000 IU urokinase, i.e., with a concentration of 5,200 IU urokinase per ml of solution and with a purity of 3% IU urokinase per ml of protein present were percolated over a column of Sepharose$^R$-EACA-aprotinin. The column volume amounted to 1.5 liters. The column was previously equilibrated with a phosphate buffer at 0.02 molar concentration at a pH of 7.2. The buffer solution contained in addition 1.0 molar NaCl. The laden resin was subsequently rinsed with 3 liters of the mentioned buffer solution and afterwards with 2 liters of a 1.0 molar NaCl solution. The adsorbed urokenase was subsequently eluted by means of a solution of 1.0 molar NaCl which had been adjusted with acetic acid to a pH of 3.9.

2 liters of solution of urokinase were obtained which in all contained 15,915,000 IU urokinase which corresponds to a yield of 71.5%. The purity of the solution obtained was 61,500 IU urokinase per mg of protein present.

There is hereby incorporated by reference the entire disclosure of Swiss priority application 7197/78-7 filed June 30, 1978.

What is claimed is:

1. A process for the production of pure urokinase of high concentration and purity starting from a preliminarily purified and concentrated urokinase crude solution comprising contacting this crude urokinase solution at a pH $\geq 6$ with a porous solid matrix having a high specific area and having immobilized on the surface aprotinin by means of covalent, chemical bonds, separating off the carrier solution and subsequently eluting the adsorbed urokinase by means of an eluting agent at pH $\leq 4.5$.

2. A process according to claim 1 wherein the urokinase is separated from the crude solution affinity-chromatographically.

3. A process according to claim 2 wherein the crude urokinase solution has a concentration of 2,000 to 10,000 IU urakinase per ml of solution and a purity of 200 to 2,000 IU urokinase per ml of protein present.

4. A process according to claim 3 wherein the crude urokinase solution has a concentration of 3,000 to 5,000 IU urokinase per ml of solution and a purity of 300 to 1,000 IU urokinase per ml of protein present.

5. A process according to claim 3 wherein the porous solid matrix is a resin based on a polysaccharide, cellulose, agarose, dextran, or a copolymer addition product of a polyacrylamide with agarose.

6. A process according to claim 5 wherein the aprotinin is bound to the solid matrix either directly by covalent bonds or indirectly by a spacer which is epsilon-aminocaproic acid, divinyl sulfone or bis-oxirane.

7. A process according to claim 3 wherein the aprotinin is bound to the solid matrix either directly by covalent bonds or indirectly by a spacer.

8. A process according to claim 7 wherein the spacer is epsilon-aminocaproic acid, divinyl sulfone or bis-oxirane.

9. A process according to claim 3 wherein the solid matrix is previously activated.

10. A process according to claim 9 wherein the activator is BrCN.

11. A process according to claim 5 wherein the adsorption of the urokinase on the aprotinin takes place in a column and the column before the actual adsorption is conditioned with a liquid medium at a pH of 6 to 9 and a total salt concentration of 0.5 to 1 moles/liters.

12. A process according to claim 11 wherein the conditioning liquid contains a buffer and NaCl or KCl.

13. A process according to claim 12 wherein the buffer is a phosphate mixture or tris sodium phosphate.

14. A process according to claim 3 wherein the crude urokinase solution is adjusted to a total salt concentration of 0.5 to 1 mole/liter.

15. A process according to claim 14 wherein the salt includes NaCl or KCl.

16. A process according to claim 1 wherein the crude urokinase solution is adjusted to a total salt concentration of 0.5 to 1 mole/liter.

17. A process according to claim 16 wherein the salt includes NaCl or KCl.

18. A process according to claim 1 carried out in a separatory column and wherein after the actual adsorption of the urokinase and before the actual elution there is an intermediate rinsing of the column with a 0.5 to 1 molar NaCl solution to remove protein from the separatory column and wherein the intermediate rinsing is continued until optical purity is obtained as shown by substantial optical inactivity at 280 nm.

19. A process according to claim 3 wherein after the actual adsorption of the urokinase and before the actual elution there is an intermediate rinsing of the column with a 0.5 to 1 molar NaCl solution to remove protein from the separatory column and wherein the intermediate rinsing is continued until optical purity is obtained as shown by substantial optical inactivity at 280 nm.

20. A process according to claim 3 wherein the elution is carried out at at pH of 2 to 4.5 and a salt concentration of 0.5 to 1 molar.

21. A process according to claim 20 wherein the salt is NaCl or KCl.

22. A process according to claim 21 wherein the pH is adjusted with acetic acid or HCl.

23. A process according to claim 1 wherein the elution is carried out at a pH of 2 to 4.5 and a salt concentration of 0.5 to 1 mole/liter.

24. A process according to claim 21 wherein there is employed an aminocarboxylic acid as an elution aid in the elution.

25. A process according to claim 24 wherein the aminocarboxylic acid is lysine or arginine.

26. A process according to claim 23 wherein there is employed an aminoacid as an elution aid in the elution.

27. A process according to claim 8 wherein the spacer is divinyl sulfone or bis-oxirane.

28. A process according to claim 27 wherein the spacer is divinyl sulfone.

29. A process according to claim 27 wherein the spacer is bis-oxirane.

30. A process according to claim 19 wherein the aprotinin is bound to the solid matrix by a spacer which is epsilon-aminocaproic acid, divinyl sulfone or bis-oxirane.

31. A process according to claim 30 wherein the adsorption of the urokinase on the aprotinin takes place in a column and the column before the actual adsorption is conditioned with a liquid medium at a pH of 6 to 9 containing a buffer and NaCl or KCl, the total salt concentration being 0.5 to 1 mole/liter.

32. A process according to claim 31 wherein the spacer is divinyl sulfone or bis-oxirane.

33. A process according to claim 30 wherein the spacer is divinyl sulfone or bis-oxirane.

34. A process according to claim 31 wherein there is employed an aminocarboxylic acid as an elution aid in the elution.

35. A process according to claim 34 wherein the spacer is divinyl sulfone or bis-oxirane and the aminocarboxylic acid used as an elution aid is lysine or arginine.

* * * * *